United States Patent
Plastow et al.

(10) Patent No.: US 7,229,764 B2
(45) Date of Patent: Jun. 12, 2007

(54) SYSTEM FOR TRACING ANIMAL PRODUCTS

(75) Inventors: Graham S. Plastow, Abingdon (GB);
Alan J. Mileham, Berkeley, CA (US);
Todd Wilken, Franklin, KY (US);
Christy Gladney, Berkeley, CA (US);
John Bastiaansen, Rosmalen (NL)

(73) Assignee: Pig Improvement Company (UK) Ltd. (GB)

( * ) Notice: Subject to any disclaimer, the term of this patent is extended or adjusted under 35 U.S.C. 154(b) by 600 days.

(21) Appl. No.: 10/409,528

(22) Filed: Apr. 8, 2003

(65) Prior Publication Data

US 2003/0228604 A1    Dec. 11, 2003

Related U.S. Application Data

(60) Provisional application No. 60/370,870, filed on Apr. 8, 2002.

(51) Int. Cl.
*C12Q 1/68* (2006.01)
*C12P 19/34* (2006.01)
*C07H 21/02* (2006.01)

(52) U.S. Cl. .......................... 435/6; 435/91.2; 536/23.1

(58) Field of Classification Search .................. 435/6, 435/91.2; 536/24.33, 24.31, 23.1
See application file for complete search history.

(56) References Cited

U.S. PATENT DOCUMENTS

| 5,292,639 | A | 3/1994 | Beitz et al. |
| 6,238,863 | B1 * | 5/2001 | Schumm et al. ............ 435/6 |
| 6,287,254 | B1 | 9/2001 | Dodds |
| 2002/0012934 | A1 | 1/2002 | Meghen et al. |
| 2002/0022772 | A1 | 2/2002 | Dodds |

FOREIGN PATENT DOCUMENTS

WO    WO 9839475 A2 *    9/1998
WO    PCT/US03/10699    12/2003

OTHER PUBLICATIONS

ABI Prism Genotyper® 3.7 NT Software User Manual (2001).

* cited by examiner

*Primary Examiner*—Suryaprabha Chunduru
(74) *Attorney, Agent, or Firm*—McKee, Voorhees & Sease, P.L.C.

(57) ABSTRACT

The present invention provides a genetic testing system that ensures complete traceability of animals and food products and involves a method of uniquely identifying animals for data collection, records management and retrieval purposes involving a novel method of genetic analysis using individual DNA fingerprinting of parentage of individual animal to effectively provide for full traceability of animals from birth to consumption.

16 Claims, 1 Drawing Sheet

SYSTEM FOR TRACING ANIMAL PRODUCTS

CROSS REFERENCE TO RELATED APPLICATIONS

This application claims benefit under 35 U.S.C. § 119(e) of provisional application No. 60/370,870 filed Apr. 8, 2002.

FIELD OF THE INVENTION

This invention is concerned with a genetic testing system that ensures complete traceability of animals and food products. The present invention relates generally to a method of uniquely identifying animals for data collection, records management and retrieval purposes. More specifically, the present invention relates to a novel method of genetic analysis using DNA fingerprinting, in a cost-effective manner, to provide full traceability for the animal production chain.

BACKGROUND OF THE INVENTION

The present invention relates to a method of uniquely identifying animals for data collection, records management and retrieval purposes in an accurate and cost-effective manner. Animal identification and registry has been an area of increasing concern over recent years. Generally speaking, animal identification and registry involves collecting data for each animal throughout its entire life cycle such that individual characteristics and the history of the animal can be tracked. This data may include, but is not necessarily limited to, date and place of birth, ancestry, sex, geographic movement, health and treatment history, and other production records. The livestock and food processing industries, in particular, have been heavily involved in this area in an effort to increase productivity and profitability in livestock management, as well as develop a strategy for identifying, tracing and managing the risks in the area of food safety and infectious disease outbreaks in livestock. Health and safety considerations demand that the origins of food products should be transparent. In addition, consumers now demand and some countries now require that the origins of meat products should be traceable so that quality assurance audits and monitoring procedures can be effectively and reliably carried out. A paper-based recording or tracking system would be sufficient to trace meat products back to the system or farm of origin. Nevertheless, papers may be lost, labels deteriorate on storage in a freezer and recording errors are made. The claimed system has the advantage that if a result is doubted or controversial, the samples in question can be retested by an independent third party. A significant challenge exists, however, in that there is currently no uniform system for identifying and tracing animals with sufficient specificity. Instead, a multitude of animal identification and registry conventions have evolved over time which vary widely depending upon such factors as the geographic location of the livestock operation and/or the manufacturer of the particular animal tracking system. One example is the lack of uniformity based on geographic location that is evident in the United States wherein each state determines its own animal identification scheme for livestock farms located within the state. Another example is, at present, various methods and combinations of methods are used in an attempt to ensure the identity and source of meat products through batch or consignment basis whereby batch/consignment numbers are applied to the batches/consignments from the source, through the slaughter process to the consumer. However, these examples demonstrate how current methods are time consuming, cumbersome and require considerable resources from farmers, processors and government or other agencies. Thus, this lack of uniformity is problematic in that it becomes increasingly difficult to trace back information concerning a specific animal. The usefulness of the collected data is thus compromised thereby undercutting such goals of the industry as increasing productivity and tracing the animal through its entire life cycle. It also increases the time required to trace back human exposure and potential issues of food safety while limiting the spread of infectious diseases which in certain circumstances, can lead to additional exposure to preventable health risks for humans and the spread of confinable diseases for animals which in turn could lead to the disposal of large numbers of animals. Managing the risk is clearly associated with data collection and information management systems that a well run animal operation should already have in place.

The capability to identify and track food products through the food chain at the retail level back to the farm or production system of origin is becoming a required process to address human safety issues. The importance of a system to trace food products is illustrated by many recent examples including problems with residues in fruit and vegetables, dioxin in poultry and *E. coli* 0157 contamination and bovine spongiform encephalopathy (BSE) in beef products. It is also increasingly a requirement from retailers in order to guarantee the wholesomeness of the food product to their customers. It can be seen that presently and in the future there is an increasing requirement to verify the quality of products. The present invention fulfills this long-standing need and desire in the art.

As genetic and genomic research expands its influence to food production there is a requirement to maintain the integrity of the chain so that the benefits of selecting specific genotypes are taken through the chain to the point where the benefit can be exploited. Today, it is possible to select for specific alleles of genes in cattle and pigs that result in meat with improved meat or eating quality as judged by the processor and consumer. Thus, it is likely that these alleles/genes will be specified and that members of the chain will require confirmation that resulting claims can be verified. There is presently a need to positively identify the genetics that are said to be part of a program or package formulated to deliver specific carcass characteristics and meat quality attributes.

It is currently possible to put in place such a traceability system using paper or electronic passports that will trace an individual animal from birth to slaughter and link to tags or other forms of animal identification such as retinal imaging. However, these systems can be subject to fraud, although technology is being developed to link the two components (passport and animal) together. Nonetheless, these processes and the technology available today can only follow the carcass to the breaking table; the point where the animal is split up into primal cuts, joints etc. Once these primals are distributed to the different boning tables, product identity and the passport is lost at least from an individual carcass perspective. Lots or batches can still be contained although a clear separation is difficult to maintain between these lots and is subject to error and this adds significantly to the cost of production. In addition, the dissemination of the product to other plants for further processing also increases the problem.

There is a need to develop genetic data in a cumulative, comprehensive, and dynamic system of database management to thereby enhance the health predictability, and longevity of animals. The claimed system has the distinct advantage of using DNA information to trace meat products to the system or farm of origin. In the present invention a method of using DNA markers is presented as a means to identifying individual animals by obtaining genotypes of all prospective parents as references to be entered into a database and then comparing genotypes of offspring samples to this database to identify the prospective parents for each offspring. Similarly, parentage analysis using DNA markers can be used in a system to identify the source of carcasses and individual cuts of meat (offspring) to a specific farm (parents). The present invention is less costly than existing DNA tracing systems based on identity as the present invention does not have to keep samples of all slaughter animals, nor DNA fingerprint all slaughter animals. In the future, if cloning is ever used in the farming industry, the claimed system would also be effective provided that the given clones were unique to a particular system/farm.

For the foregoing reasons, there is a need for a system which traces animals through an efficient and cost-effective DNA marker method. The method of the present invention comprises the first step of providing a unique universal identification system for animals, such as pigs, that enables the identification and management to track food products through the food chain.

Accordingly, a primary objective of the invention is a method of genetic analysis using DNA fingerprinting to provide full traceability for the animal production chain whereby the collection of parentage samples is required and the collection of samples of the offspring groups provides for a necessary database for future use.

Another objective of the invention is the health profiling of an animal that determines characteristics of that animal through parentage DNA profiling.

A further objective of the invention is health profiling of an animal that comprises genetic data of animals enabling health assessment data of animals thereby to permit an analysis predicting health, disease, and disorder probabilities.

Yet another objective of the invention is a method for utilizing the genetic data of animals to provide a universal database enabling a traceability system for the entire production chain.

The method and means of accomplishing each of the above objectives will become apparent from the detailed description of the invention which follows. Additional objectives and advantages of the invention will also be set forth in part in the detailed description and in part will be obvious from the examples, or may be learned by the practice of the invention. The objectives and advantages of the invention will be obtained by means of the instrumentalities and combinations, particularly pointed out in the claims of the invention.

SUMMARY OF THE INVENTION

The present invention discloses a method and a system for identifying animals that enables DNA marker technology to trace meat products using a parentage system to be utilized in order to cost-effectively provide full traceability for the animal production chain to the system or farm of origin. This system requires DNA markers to be used as a means to identify parentage of individual animals, identify the source of carcasses and individual cuts of meat, and the precise system or farm of origin for the animals selected. The collection of parental samples, the collection of offspring groups, grandparent samples, statistically-based sampling at various control points through the chain and DNA verification systems to demonstrate the origin, both genetic and by location of samples throughout the chain is required to effectively implement and verify the present invention. The genotype information will be entered and then uploaded by means well known to those in the art such as file uploads or database link. The genotype and sampling information will then be extracted from the database and run through the data-analysis software described in the Examples. For parentage analysis this can be done using available commercial programs known to those skilled in the art. The system can be further enhanced through integration with information management technology such as using web-based result reporting and identification By creating this system utilizing these discreet and distinct components the present invention provides cost-effective identity preservation for animal products. This system has specific advantages over existing systems in terms of the ease of use throughout the production chain and the cost of implementation. In addition, the system can be tailored to fit the requirements at each point in the chain thereby increasing the robustness of the system with respect to fraud. These factors increase utility and are important in ensuring the adoption and implementation required by the participants in the chain. Further aspects, features and advantages of the present invention will be apparent from the following description of the presently preferred embodiments of the invention given for the purpose of disclosure.

DETAILED DESCRIPTION OF PREFERRED EMBODIMENTS

Figure 1:
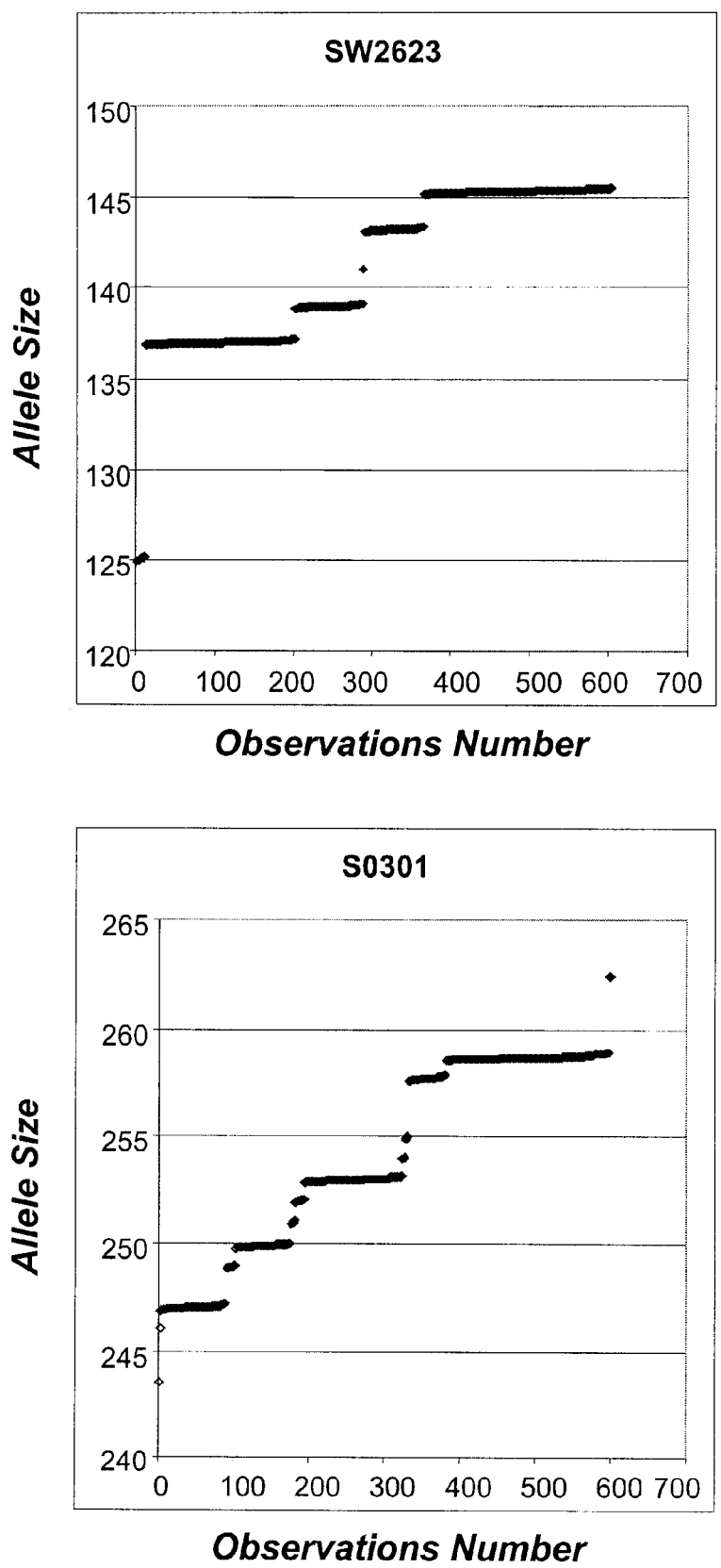
FIG. 1 demonstrates sorted allele size distribution for markers SW2623 and S0301. The X axis=observations number and the Y axis=allele size as called by Genotyper® software.

The present invention utilizes the accuracy of DNA technology to teach a system of traceability to the individual animal or group of animals such as a production unit back to the system or farm of origin. This system enables the health professional, producer, processor and retailer to obtain information about specific animals and their offspring in order to estimate the presence and prevalence of disease or disorder, identify desirable heritable traits, and to promote a detailed uniform system.

Living organisms offer a unique individual fingerprint in their DNA. DNA therefore provides the possibility to maintain traceability from birth to consumption. However, from a practical point of view, the current use of DNA technology for this purpose is a tremendous task requiring intense management and relatively high cost as it is based on identity testing. Although identity-based systems are being developed for beef and lamb such as IdentiGen in Ireland and Easi-trace in New Zealand, these are not truly applicable to pigs. Sample collection, genotyping, data analysis, cost versus the value of the carcass and the sheer numbers of animals that would need to be typed have prevented the application of this technology in species such as dogs, cattle, cats, horses and sheep.

The method of the present invention provides the ability to uniquely identify animals in a uniform and consistent fashion using DNA technology that allows for quick and easy access to the data collected and thus the ability to trace meat products back to the system or farm of origin. The claimed traceability program can be set up with the use of between 10 and 100 microsatellite markers, but preferably between 20 and 50 microsatellite markers to identify the animal from outside the controlled system or farm of origin. The present invention thus minimizes the amount of time required to trace back diseases, thereby reducing the risk of having disease-free animals become infected, and reducing the associated health risks to humans. The method of the present invention is also advantageous in that it provides the ability to identify animals regardless of the manufacturer of the particular animal tracking system employed by the livestock concern. The present system will utilize a database and sample storage system that can be bundled together in an easy to use format using readily available software for the analysis. Further, the claimed invention is less costly than previously utilized DNA systems based on identity as the present invention does not require that samples of all slaughter pigs be kept, nor all animals must be DNA fingerprinted. This is due to the fact that the claimed system is based on parentage and therefore can be done using only post slaughter meat samples. Another unique advantage of the present invention is the fact that as the effective number of genetically different sires in the system or farm would be significantly reduced, thereby allowing fewer markers and thus the claimed traceability system would significantly reduce costs. This allows the livestock producer(s) and food processors to more easily collect and track data on an individual animal during its life cycle providing for increased productivity and protecting the general health and well being of workers, consumers and animals.

The present invention is a method for identifying the animal from which a food product is derived comprising sampling the animal tissue, extracting genetic material from the sample, carrying out a genetic analysis on the extracted genetic material and encoding the results of the molecular genetic analysis, entering the sample information and coded genetic analysis onto a database and allowing for the sample information to be searchable in order to discern the molecular genetic analysis of an animal. The present invention discloses an improved procedure for DNA marker analysis using parentage samples, reference samples of offspring and other forms of nucleic acid sequence analysis which enables the rapid and simultaneous analysis of a large number of DNA markers. The system claimed is unique in that it is based on paternity. This results in a very cost-effective system as far fewer sires are in use in the industry than dams. Provided a group of sires are used exclusively within a system or farm, then meat from slaughter pigs, for example, derived from that system or farm can be effectively traced back to the system or farm. Nonetheless, the claimed invention is equally applicable for a system or farm that shared boars (through AI) with other systems or farms. In this instance, the system would be based on maternity. The amount of testing (fingerprinting) of the reference set would need to be increased in this situation as this would now comprise all of the dams in the system or farm (as opposed to the sires) and thus the overall costs would increase somewhat, but the claimed invention would allow for an improved capability to trace meat or meat products unequivocally to their system or farm of origin. The expected high information content of this system will facilitate many kinds of genetic analysis and enable an improved and more uniform traceability system that will provide for different traceability options such as partial traceability if warranted. This invention also provides an improved method for obtaining nucleic acids extracted from different biological samples. The identity of individuals is assessed through "DNA typing" and genes associated with the specific individual are then identified and mapped to specific sites on the chromosomes. In this process of DNA fingerprinting, variations in the DNA sequence of different individuals of a species (DNA sequence polymorphisms) are revealed by differences in the quantitative pattern of binding of DNA fragments prepared from different individuals to an array of a few hundred to a few thousand oligonucleotides probes.

The system of the present invention is set up according to the requirements of the production chain, but a basic unit is a production unit such as an individual farm. Female animals (dams) are selected to stock the system and a DNA sample is taken and stored as part of the individual's passport providing a reference sample as well as identification records (such as ID tag number etc.). It will be realized by those skilled in the art that a variety of methods can be used to link the passport to the animal including electronic transponders, retinal scanning systems or iris scanning systems. In turn, male animals (sires) are selected to be mated to these dams. These male animals will typically be selected to be used uniquely within the system or in related systems. As with the dams, samples of the sires are taken for reference. DNA profiles are generated for these parent animals using any DNA marker based system that provides the necessary discriminatory power. One example, it may be necessary that sires are segregated for use only within a single production system and relies on the practice that dams are only located in specified farms or in a particular farm for a specified time. The markers are polymorphic thereby giving each different individual a uniqueness that is identifiable and traceable. Such markers can be selected from microsatellites, specific single nucleotide polymorphisms (SNPs), AFLP markers or deletions or insertions of all, or part of, the genomic DNA sequence. The type of marker is not particularly important, but these markers will be selected to deliver the most efficient system. For example, by using highly polymorphic microsatellite markers it is possible to easily verify parentage of an animal if the samples of parents are also available. In some situations specific SNP markers can provide very efficient first stage discrimination. A pig producer, for example, may wish to utilize Duroc sires as they are preferred in some markets for meat quality attributes, the Duroc pig has a specific polymorphism in the MC1R gene which is diagnostic for this breed, so that a pig from this system must contain at least one Duroc allele. Any sample that is negative for this Duroc allele can be excluded from the system. This approach can be applied for alleles of other genes that are specified such as in the United States some processors specify the absence of the Halothane gene. In such a system any pig carrying the Halothane gene can be excluded. This is an important feature of the system of the present invention since the specified genotype of the individual will be used to demonstrate compliance with system requirements and it is likely that in the future products (meat) resulting from the animal will be valued based on the specific genotype. It will be apparent to those skilled in the art what techniques are necessary in order to identify the markers and it is not intended that the invention be limited by such illustrative embodiments or mechanisms, and that modifications can be made without departing from the scope or spirit of the invention, as defined by the appended claims.

The present invention's traceability system also has other significant benefits. For example, the sires of any pigs born in the system or farm with genetic defects can immediately be traced. Culling these boars (and dams if warranted) present the advantage of reducing the incidence of congenital defects in the system or farm. The following is just one example of the claimed use of DNA fingerprinting tools to identify an AI boar carrying a previously unknown genetic heart defect. Piglets with a condition known as "football" pigs were noted on farms using semen from a particular AI stud, but because the stud used the semen from several boars to make their commercial AI doses, no one could identify if one or several boars were responsible, if this was an infectious disease, or if it was caused by something in the environment. The claimed invention using the system based on parentage and traceability tools allowed it to be shown that a single boar had sired the affected piglets.

Another example of the benefits of the claimed system is the ability of the fertility of sires to be monitored in a system or farm. For example, this is achieved by sampling and fingerprinting pigs after slaughter and then comparing real proportion of offspring sired by a given boar to the estimated proportion of offspring he would be expected to have sired based on his known contribution to the AI doses used in the system or farm. This allows for previously undiagnosed sub-fertile or infertile boars to be identified and culled. This also provides the distinct advantage of raising the overall fertility of the system or farm. Currently boars on a stud are monitored for the quality of their semen in terms of sperm concentration, motility and morphology. If their semen is mixed with that of other boars in producing AI doses, then their fertility cannot be checked. Many conditions are known where sperm concentration, motility and morphology of male mammals can look normal, but the male has poor fertility (e.g. reciprocal translocations, mutations in genes involved in sperm/egg recognition etc.).

The claimed traceability system also has the unique ability to devise system based on grandparents and great grandparents as opposed to using paternity or maternity. This allows for a distinct advantage of requiring a much reduced number of reference animal fingerprints in the database which would also lead to lowered costs. This approach does require a different approach because an individual does not have to share an allele with its grandparent at each locus. Therefore exclusion of a candidate grandparent is not possible in the same way a candidate parent can be excluded when there is no matching allele at a locus. The claimed invention allows for an exclusion approach to be taken if the pair of paternal grandparents or maternal grandparents is sampled. An individual must have at least one allele in common with the set of four alleles in the two grandparents on the father's side, and one allele with the set of four alleles in the two grandparents on the mother's side. Exclusion probabilities are calculated similar to the parent/offspring situation. For example, for a two allele marker you would have the following:

|  | Grand parent alleles | | | | |
| --- | --- | --- | --- | --- | --- |
| Grandoffspring alleles | 1111 | 1112 | 1122 | 1222 | 2222 |
| 11 |  |  |  |  | 0.015625 |
| 12 |  |  |  |  |  |
| 22 | 0.015625 |  |  |  |  |

Only the combination of 1111 grandparents with a 22 grandoffspring or 2222 grandparents with 11 grandoffspring would exclude this combination of the two grandparents.

The exclusion probability for unrelated individuals (using a marker with two equally frequent alleles) is:

$$2\times(\text{freq 1})^4\times(\text{freq 2})^2 = 2\times0.5\times0.5\times0.5\times0.5\times0.5\times0.5 = 2\times0.0625\times0.25 = 0.01325$$

Each of the two grandparents in the pair with 1111 alleles could still be a true grandparent together with another candidate grandparent therefore it is necessary for all possible combinations of grandsire+grandam to be tested.

There have been other options to assign grandparents or great grandparents to an individual, one at a time. In a recent publication, Milligan (2003) developed a likelihood estimator for the relationship between any two individuals based on marker genotypes only and reviewed other methods. Milligan, Brook G., Maximum-Likelihood Estimation of Relatedness, *Genetics;* 163, pages 1153-1167 (2003). It was shown that the likelihood method was effective with relationships as distant as first cousins, which have the same degree of relationship as a great grandparent and its great grandoffspring, and even with unrelated individuals. In the claimed traceability system it will be know which generation an individual belongs to. This is extremely useful for pairs of individuals with relationships of 0.25, for example, half-sibs. The present invention permits one to keep track of which generation a sampled individual belongs therefore there is no need to distinguish between a halfsib and a grandparent. It will be necessary to distinguish between a relationship of 0.25 (true grandparent) and 0.125 (full sib to true grandparent), nonetheless, the increased number of markers needed to perform this, somewhat larger than 30 markers, will be simple to obtain. In addition, a reduced number of reference genotypes will be needed, resulting in a less expensive system overall. For grandparent analysis the analysis can be done by a computer program that is similar to the aforementioned for parentage analysis. The ability to devise such a system is yet another unique embodiment of the claimed invention.

In the system of the claimed invention samples are also collected from progeny, however, in this case it is not necessary to type them. Rather these samples are stored as reference samples should problems be encountered or a greater level of verification is required. In some situations, it will not even be necessary to code these individually but instead they can be grouped by birth group such as litter in pigs, building, birth day or week or month etc. This is an important and unique advantage of the present invention over previous products where all individuals are required to be typed.

For example, if an individual piece of meat or retail pack needs to be tracked back to the system, such as a result of foreign body product contamination or other such problem, it can he done efficiently as part of a two stage system. Information on the lot or system from the pack or sales document is combined with a biological sample to provide DNA for analysis and is sent to the reference laboratory. It is here the DNA profile is determined and it is matched to the parent samples in order to determine if there is a match to the system. This describes the claimed form of a parentage test. It should be noted that this can be further refined based on birth and/or production date of the animal. If there is a match to the system, it will result in the identification of potential batches such as litters for pigs. Once this is done then a more accurate match can be made on an individual basis in a much more efficient and cost-effective manner than individually typing every carcass. In the present invention the sample is searched against individuals for specific identity. The probability that a match is obtained with a non-identical individual will be infinitesimal by using this approach.

The system can be further enhanced through integration with information management technology such as using web-based result reporting and identification. Sample information may be entered via file upload or web-interface or other known means in the art. The sample information will include, but is not limited to, sample date, animal location (e.g., farm number, pen), animal status (e.g. parent, slaughterpig), sample shipping information and sample storage information. The genotype information will be entered and then uploaded by means well known to those in the art such as file uploads or database link. The genotype and sampling information will then be extracted from the database and run through the data-analysis software described in the Examples. For parentage analysis this can be done using available commercial programs known to those skilled in the art. For grandparent analysis the analysis can be done by a computer program that is similar to the aforementioned.

It can be seen that by using this system a cost-effective approach to full food chain traceability can be obtained that is not possible by simply using individual identity. The system of the invention does require a high level of organization as well as the ability to combine specific animal genotypes (selected parents) and different DNA marker systems and data management and transfer technology so as to be able to deliver an effective system for species harvested in high volumes and with relatively low carcass value such as the pig as in comparison to the bovine. This system is unique and the invention described herein represents a major advancement for the traceability of animal products in the production chain, in particular for high quality meat products. In addition, it can be seen that the potential advantages may also apply for higher value, lower volume animal products such as beef.

The present invention teaches a number of benefits that are obtained by those implementing the claimed invention. These include a greater capability to meet current and future regulatory requirements, improvement of the image of the industry, credibility through transparency of industry to ensure food safety and also verify product claims such as quality of food product due to specific genotype, statement of security of the food source, verification of claims to a farm system for example, organic, welfare friendly and the like and enhanced product value due to the presence of specific genes (as demonstrated with genetic markers) that indicate a higher degree of quality and value or demonstrate conformance to specification.

In conclusion, the present invention discloses a system for tracing an individual animal from birth to consumption. Further, performing such an objective is taught by the present invention through a precise and cost-effective method thereby allowing for the use of enhanced genetic and genomic research data and improvement of human food safety issues.

Definitions

For purposes of this application the following terms shall have the definitions recited herein. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUM Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

As used herein, an "animal" is any species whose meat is commercially sold either for human consumption or for animal consumption. Animal species included, but not limited to, are bovine, fish, goats, ovine, porcine, poultry, shellfish and shrimp.

As used herein, a "basic unit" is a production unit such as an individual farm whereby the dams and/or sires are located in specified farms or in a particular farm for a specified time.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

EXAMPLES

Introduction

A pilot project for a traceability scheme was designed around two sow units (SU1 and SU2) that both utilize semen from a common boar stud (BS1). The BS1 boar stud houses approximately 25 PIC line 337 sires. SU1 and SU2 are both 600 sow units (farrowing 25 litters/wk) that utilize PIC C22 parent females. Both farms maintain good on-farm production records.

Tissue samples were also taken from unrelated PIC337× C22 slaughter pigs originating from an unrelated production system (System II). These samples were utilized as a negative control against pigs originating from the system described above.

DNA markers are proposed as a means to identifying parentage of individual animals. In addition, parentage analysis by DNA markers was to be evaluated as a system of identifying the source of carcasses and individual cuts of meat to a specific farm.

MATERIALS

Samples

On farm sampling was performed to obtain DNA samples from the 21 Boars present at BS1 at the time of sampling and from 13 litters (4 piglets each) with their sows for each of the two sow units, SU1 and SU2. From System II, 50 DNA samples were obtained on pigs unrelated to the test system.

At the slaughter plant, samples were taken from carcasses identified as supplied by SU1 and SU2. Samples of skin and loin were taken from 50 carcasses from each of the farms and 15 samples of ham for each farm. On both farms additional sows were sampled that were expected to be parents of the sampled carcasses.

TABLE 1

Breakdown of the number of samples by source (farm) and type of animal or type of cut sampled.
Total samples:

| Animal source | boars | Sows a | Sows b | offspring | skin | loin | ham |
|---|---|---|---|---|---|---|---|
| BSI | 21(+2) | — | — | — | — | — | — |
| SU1 | — | 14 | 119 | 56 | 50 | 50 | 15 |
| SU2 | — | 14 | 50 | 56 | 50 | 50 | 15 |
| System II | — | — | — | 50 | — | — | — |

Markers

A 9 marker set published by PE AgGen for parentage analysis in pigs was used as the basis for a 12 marker set. Twelve markers is the current limit for a single run on the ABI genotyper (4 colors×3 marker size ranges). Two of the markers in the PE AgGen set were not used. SW2160 is the 5th marker in its size range, and SW840 is linked to another marker in the set. Five markers were added to the AgGen set from MS markers used in the European Biodiversity project (http://databases.roslin.ac.uk/pigbiodiv). Three criteria were used for these additional markers. First, they had to be unlinked to any of the markers already in the set of 12. The second criteria was that the polymorphism was informative averaged over 9 PIC lines. Third, their size range had to fit into one of the remaining positions (maximum of 4 in the same range).

The final set of markers is as follows:

TABLE 2

Microsatellite markers used for parentage analysis.

| Color | Marker | Size Range | SSC | ~cM |
|---|---|---|---|---|
| Tet | SW1430 | 159–181 | 1 | |
| Fam | SW2623 | 123–149 | 2 | 10 cM |
| Fam | S0226 | 169–231 | 2 | 75 cM |
| Fam | SW72 | 100–118 | 3p | |
| Tet | S0097 | 208–248 | 4 | 120 cM |
| Fam | S0301 | 254–266 | 4 | 27 cM |
| Ned | SW122 | 110–122 | 6 | |
| Vic | TNFB | 156–216 | 7 | |
| Ned | SW857 | 144–160 | 14 | |
| Tet | SW936 | 80–117 | 15 | |
| Ned | SW2411 | 179–229 | 16 | |
| Vic | SW24 | 89–121 | 17 | |

As shown in Table 2, there are not exactly 3 markers per color. This happened because one of the markers was already available with the Blue dye (Fam) and did not overlap with the other 3 in this color. Chromosomes 2 and 4 each have 2 markers on them but these are at least 65 cM apart and therefore essentially unlinked.

Software

Genotype analysis may be performed using Genotyper® software as provided with the ABI machine to call the allele sizes for each of the markers. This software is constructed to be completely automatic but a manual check of its results is necessary at this time. The Genotyper® output will list the allele sizes in basepair units, up to two decimals.

Parentage analysis: The linkage software list at Rockefeller University was searched for parentage analysis software. The following applications were found and may be utilized in the present invention: SALP, Borel, Cervus, Newpat/identity, Kinship). Preferably Cervus should be used as it works on PC and support is available if needed. Cervus can easily handle missing genotypes, genotype errors and will therefore work well on real data. In addition to data analysis Cervus has some simulation tools which allows the prediction of power of a certain marker set for specific population parameters.

Allele bins: A SAS application has been written to recode the allele scores from the Genotyper® output to integer allele numbers based on observed ranges fro each of the alleles. Results outside the predefined ranges or otherwise unusable genotype calls are output in a list for further investigation. The SAS application writes all the usable genotypes to a Cervus input file and/or to an easy to interpret output file for users.

Genotype storage: This is currently done in Excel master files. Presently an Access database for storage of genotype results may be utilized. In the future, the Access prototype can be programmed into an Oracle database. For genotype storage the database will be simplistic. Additional features like sample storage information can be added to this when necessary.

RESULTS

Genotyping

Genotyping was done for the 12 markers in Table 2 on all 612 samples in Table 1. One of the markers, S0097, gave technical difficulties with PCR amplification and/or genotyping which made it impossible to call the allele sizes with the Genotyper® software nor by human intervention.

Genotype results for 303 samples were used to define the allele bin ranges. The 606 alleles from these genotypes were sorted by size (from the Genotyper® output) and plotted as shown in FIG. 1 for SW2623 and S0301.

The observed bin ranges of SW2623 are easily interpretable with steps of 2 basepairs between the different ranges. The beginning and end points of each range were extended by 0.10 basepair and then used as cut-off points in the allele binning SAS application.

S0301 is included here to illustrate a problem with this marker. Between allele sizes 249 and 255 there are observations at 1 basepair intervals. This was observed for a few other markers as well, in which case it could be determined that two observations within 1 basepair were really the same allele and could be binned in the same range. For instance for TNFB a Genotyper® call of 161 or 162 can always be recoded to a 162 allele because the 161 is just an infrequent "mistake" of the system. For S0301 Applicants were not as fortunate as there are several ways to end up with a 249 Genotyper ® call (a real 249 allele, a mislabeled 250 allele or a 247/251 heterozygote) which cannot be distinguished between unambiguously. The S0301 has therefore been removed from parentage analysis. Allele bin range results are listed in Table 3.

Two sires at BS1 had been sampled twice and therefore 2 of the samples (BVS19 and BVS21) were removed from the analysis after identical genotypes patterns were found for sires 1 and 21 and for sires 2 and 19. This left 610 samples to be used in parentage analysis.

The proportion of missing genotypes at the start of parentage analysis was 2.4%. The majority of these were due to alleles falling outside the predefined ranges. These results can be checked individually and used to refine the allele bin ranges but this has not been done yet. 2.4% is a very low percentage already and conclusions are unlikely to be affected.

Parentage Analysis

The Trial proposal indicated 3 tests to be performed, results of which are in the candidate parents are the 21 BS1 sires plus all the sows (a and b) listed in Table 1. Because of the longer time lag between matings that produced these slaughtered pigs and sampling at BS1, a smaller percentage of the carcasses is expected to match to BS1 sires than of the offspring born at SU1 and SU2. The limited number of dams sampled at SU2 and SU1 are expected to include only a proportion of the dams that produced the slaughter pigs sampled. Also, fewer SU2 dams were sampled compared to SU1 which is reflected in the smaller proportion of matched slaughter pigs

TABLE 4

| | SU1 | | | SU2 | | | SYSTEM II | | |
|---|---|---|---|---|---|---|---|---|---|
| | | Test 2 | | | Test 2 | | | | |
| | Test 1 Pigs | Carcasses (skin) | Test 3 Meat (ham) | Test 1 Pigs | Carcasses (skin) | Test 3 Meat (ham) | Test 1 Pigs | Test 2 Carcasses | Test 3 Meat |
| BS1 sires | *47/56* | *25/50* | *9/15* | *28/56* | *23/56* | *7/15* | 13/50 | — | — |
| SU1 dams | *54/56* | *38/50* | *11/15* | 8/56 | 31/50 | 12/15 | 5/50 | — | — |
| BS1 sires + SU1 dams | *40/56* | *12/50* | *7/15* | 0/56 | 3/50 | 0/15 | 0/50 | — | — |
| SU2 dams | 11/156 | 17/50 | 9/15 | *56/56* | *28/50* | *13/15* | 7/50 | — | — |
| BS1 sires + SU2 dams | 0/56 | 1/50 | 0/15 | *23/56* | *6/50* | *1/15* | 0/50 | — | — |

Table 4. Proportion of samples from tests 1, 2 and 3 (columns) that could be assigned parents from the group of parents indicated in each row. Results in bold italics indicate that a match was expected/desirable, underlined results indicate no matches were expected/desirable.

For test 1 the offspring born on each of the 3 farms (56, 56 and 50 respectively) were to be matched with candidate parents listed in column 1 on Table 4. These are the 21 sires listed in Table 1 as well as the dams listed in Table 1 under sows-a. Taking SU1 and SU2 together, 75 out of 112 offspring or 67% can be matched with a sire present at BS1 at the time of sampling (results on line 1). In other words 33% of the offspring was sired by a different boar. This compares with a percentage of boars culled between matings and sampling of 20%.

54 of the 56 offspring at the SU1 are matched to one of the 14 SU1 sows expected to have produced them and only one of the 54 was assigned to a different sow than the one on record (results on line 2). All the offspring at SU2 can be matched to one of the 14 SU2 sows, all but 2 offspring are assigned to the sow recorded as the mother. This is a high success rate of assigning offspring to the correct sow farm (results on line 4). One drawback to this result is the assignment of 11 SU1 sows and 8 SU2 sows respectively to offspring of the wrong system. Also 5 and 7 offspring from system 2 have sows assigned from SU 1 and SU2 respectively.

The most stringent test is to assign both a sire and a dam to an offspring. This was done by assigning sires first and subsequently assigning dams while using the assigned sire as a known parent (method as suggested in Cervus documentation). This way the successful assignment of two parents is always less or equal to the proportion of offspring with an assigned sire. For SU1 offspring, two parents could be assigned to 40 out of 56 offspring (results in row 3) and for SU2 23 out of 56 had two parents assigned. In system 2 none of the offspring had both a BS1 sire and a SU1 or SU2 dam assigned, as was expected and desirable.

Tests 2 and 3 required carcasses, loins and hams, sampled at the slaughter plant and recorded as sourced from SU2 and SU1 to be matched to parents at those two farms. In this case from SU2 (28/50 vs. 38/50). The results in Table 4 support these expectations. A fairly large proportion of slaughter pigs are matched to sows from the wrong farm (lines 2 and 4) when only dams are assigned. When both parents are assigned, very few carcasses and no hams are assigned to the wrong farm source. No separate analysis was done for the loin samples. 10% of the loin samples from each farm were genotyped and compared to their corresponding skin samples. No discrepancies were found.

CONCLUSIONS

Beginning with the most promising result, 110 out of 112 piglets could be matched to at least one sow in the correct farm. This shows the accuracy of the markers in this project as here Applicants are most certain about having sampled all the candidate parents. It is known that at least 5 sires were culled between matings and sampling of the offspring, which means that not all the sires are included in this test. Matching the carcasses to sows at the two farms within the system Applicants know that only part of the sows were sampled, 133 and 64 out of 600 respectively. Also, the presence of additional candidate parents increases the chance of a random match between a carcass and a sow from the wrong farm (false positives).

The results obtained allow one to predict the power of the Traceability system as applied here in this trial system, and to make predictions of its performance in other (larger) systems.

Effect of the Current System

The main parameter in a traceability system is the probability of exclusion (Pe). This is the probability that a set of markers will tell you that a randomly chosen candidate parent is not the real parent of an offspring. This is easiest explained for a situation with a single marker with 2 alleles (Table 5). There are 2 parent offspring combinations, marked in italics, that will exclude a candidate as this offspring's parent. The frequency with which this occurs for a random pair of 2 animals is $2/16$ or 0.125. The exclusion probability of this marker is therefore 12.5%. This 2 allele marker is obviously not very informative which is why microsatellite markers are used. The exclusion probabilities when using 1, 2, etc. up to 10 markers, is given in Table 6.

TABLE 5

Percentage example with genotypes in bold and frequencies as fractions.

|  |  | candidate parent | | |
|---|---|---|---|---|
|  |  | 1/4 | 1/2 | 1/4 |
| offspring |  | 11 | 12 | 22 |
| 1/4 | 11 | 1/16 | 1/8 | *1/16* |
| 1/2 | 12 | 1/8 | 1/4 | 1/8 |
| 1/4 | 22 | *1/16* | 1/8 | 1/16 |

TABLE 6

Exclusion probabilities and average number of candidate parents assigned or observed.

| Number of markers | Pe first parent | Pe second parent | Predicted # dams assigned per piglet | Observed # dams assigned per piglet |
|---|---|---|---|---|
| 1 | 0.431 | 0.608 | 16.4 | 11.2 |
| 2 | 0.607 | 0.798 | 11.6 | 9.7 |
| 3 | 0.753 | 0.909 | 7.7 | 6.7 |
| 4 | 0.879 | 0.971 | 4.3 | 4.4 |
| 5 | 0.931 | 0.989 | 2.9 | 3.4 |
| 6 | 0.95 | 0.994 | 2.4 | 2.7 |
| 7 | 0.964 | 0.996 | 2.0 | 2.4 |
| 8 | 0.978 | 0.998 | 1.6 | 1.8 |
| 9 | 0.982 | 0.998998 | 1.5 | 1.7 |
| 10 | 0.988 | 0.999532 | 1.3 | 1.4 |

The Pe value for the first parent is used to predict the average number of dams assigned, out of 28 candidates, to each piglet. The predicted values hold up very well when compared to the observed values in the last column. The Pe value for the second parent will be used to make predictions for larger systems later on. This second parent Pe is the probability of excluding a random animal from being the second parent when the genotype of the first parent is known.

Because the predicted values follow so closely the observed results, Applicants can make predictions for a larger Traceability system. A larger system means that there are more candidate parents. The higher the number of candidate parents, the smaller the probability that one can exclude all (but one) of them with a given number of markers. If the Pe of a marker system is 95% then that means that each false candidate has a 95% chance of being excluded. It also means that 1 in 20 candidates will be assigned (not excluded) as a possible parent, so that in a system with 10,000 sows one will end up with 500 candidate parents. To gauge the value of a set of markers in a specific system Applicants define $Pe_x$, where x is the number of candidate parents.

TABLE 7

$Pe_x$ values for Verispeq systems employing between 5 and 50 markers. Pe values for 40 and 50 markers (first parent) or for 20 and 30 markers (second parent) are estimated, others are calculated from actual data.

| # markers | Pe | 50 | 100 | 600 | 10,000 | 20,000 | 30,000 | 40,000 | 50,000 |
|---|---|---|---|---|---|---|---|---|---|
| | | | | $Pe_x$ first parent | | | | | |
| 5 | 0.931 | 0.03 | 0 | 0 | 0 | 0 | 0 | 0 | 0 |
| 10 | 0.988 | 0.55 | 0.30 | 0 | 0 | 0 | 0 | 0 | 0 |
| 15 | 0.999195 | 0.96 | 0.92 | 0.62 | 0 | 0 | 0 | 0 | 0 |
| 20 | 0.999865 | 0.99 | 0.99 | 0.92 | 0.26 | 0.07 | 0.02 | 0 | 0 |
| 30 | 0.999998 | 0.99 | 0.99 | 0.99 | 0.98 | 0.96 | 0.94 | 0.92 | 0.90 |

TABLE 7-continued

Pe$_x$ values for Verispeq systems employing between 5 and 50 markers. Pe values for 40 and 50 markers (first parent) or for 20 and 30 markers (second parent) are estimated, others are calculated from actual data.

| # markers | Pe | 50 | 100 | 600 | 10,000 | 20,000 | 30,000 | 40,000 | 50,000 |
|---|---|---|---|---|---|---|---|---|---|
| 40 | 0.9999999 | 0.99 | 0.99 | 0.99 | 0.99 | 0.99 | 0.99 | 0.99 | 0.99 |
| 50 | 0.99999999 | 0.99 | 0.99 | 0.99 | 0.99 | 0.99 | 0.99 | 0.99 | 0.99 |
| Pe$_x$ second parent ||||||||||
| 5 | 0.989 | 0.58 | 0.33 | 0 | 0 | 0 | 0 | 0 | 0 |
| 10 | 0.999532 | 0.98 | 0.95 | 0.76 | 0.01 | 0 | 0 | 0 | 0 |
| 15 | 0.999995 | 0.99 | 0.99 | 0.99 | 0.95 | 0.90 | 0.86 | 0.82 | 0.78 |
| 20 | 0.999999 | 0.99 | 0.99 | 0.99 | 0.99 | 0.98 | 0.97 | 0.96 | 0.95 |
| 30 | 0.9999999 | 0.99 | 0.99 | 0.99 | 0.99 | 0.99 | 0.99 | 0.99 | 0.99 |

A marker system with a Pe$_{500}$ value of 95% can exclude all the candidates in a set of 500, 95% of the time. Often one will want to exclude only 499 out of 500 but the results will be very similar and the math quite a bit easier if one does the calculations for excluding all of the candidates. For a Pe of 95%, the Pe$_{10}$=(0.95)$^{10}$ or 60% but the Pe$_{10,000}$ is a number very close to zero (roughly 1.7*10$^{-233}$). The Pe$_x$ (Table 7) calculated here are based on the real Pe values observed in this trial.

The Pe$_{14}$ value for 10 markers is 84% which means that Applicants expect 16% of the piglets to be assigned a dam from the wrong farm. This is close to the observed 12% of system II piglets that have a sow assigned from SU1 or SU2 and also close to the 17% of piglets at SU1 and SU2 that had a sow assigned from the alternate farm (results in Table 3). A value for 1–Pe$_{21}$ of 22% is again close to the observed 26% of pigs in system II that get assigned a sire from BS1.

It is intended that all such obvious modifications and variations be included within the scope of the present invention as defined in the appended claims. The claims are meant to cover the claimed components and steps in any sequence which is effective to meet the objectives there intended, unless the context specifically indicates to the contrary. It is to be further understood that all citations to articles, etc., herein are hereby expressly incorporated in their entirety by reference.

TABLE 3

Allele bin ranges used in Traceability analyses.

| | allele number | observed | range | length of range | range midpoint | observed distance to next allele | defined range (=observed + or − .10) | | defined distance to next allele |
|---|---|---|---|---|---|---|---|---|---|
| S0226 | 185 | 185.03 | 185.78 | 0.75 | 185.41 | 1.29 | 184.93 | 185.88 | 1.09 |
| | 187 | 187.07 | 187.79 | 0.72 | 187.43 | 5.41 | 186.97 | 187.89 | 5.21 |
| | 194 | 193.2 | 193.88 | 0.68 | 193.54 | 5.35 | 193.1 | 193.98 | 5.15 |
| | 200 | 199.23 | 199.92 | 0.69 | 199.58 | 5.43 | 199.13 | 200.02 | 5.23 |
| | 206 | 205.35 | 205.92 | 0.57 | 205.64 | 1.77 | 205.25 | 206.02 | 1.57 |
| | 208 | 207.69 | 207.88 | 0.19 | 207.79 | 7.58 | 207.59 | 207.98 | 7.38 |
| | 216 | 215.46 | 216.07 | 0.61 | 215.77 | | 215.36 | 216.17 | |
| SW2623 | 125 | 124.97 | 125.23 | 0.26 | 125.10 | 11.55 | 124.87 | 125.33 | 11.35 |
| | 137 | 136.78 | 137.14 | 0.36 | 136.96 | 1.62 | 136.68 | 137.24 | 1.42 |
| | 139 | 138.76 | 139.08 | 0.32 | 138.92 | 1.91 | 138.66 | 139.18 | 1.71 |
| | 141 | 140.99 | 140.99 | 0 | 140.99 | 2.04 | 140.89 | 141.09 | 1.84 |
| | 143 | 143.03 | 143.37 | 0.34 | 143.20 | 1.76 | 142.93 | 143.47 | 1.56 |
| | 145 | 145.13 | 145.49 | 0.36 | 145.31 | | 145.03 | 145.59 | |
| SW72 | 103 | 102.91 | 103.37 | 0.46 | 103.14 | 7.41 | 102.81 | 103.47 | 7.21 |
| | 111 | 110.78 | 111.68 | 0.9 | 111.23 | 1.33 | 110.68 | 111.78 | 1.13 |
| | 113 | 113.01 | 113.78 | 0.77 | 113.40 | 1.26 | 112.91 | 113.88 | 1.06 |
| | 115 | 115.04 | 115.83 | 0.79 | 115.44 | 3.85 | 114.94 | 115.93 | 3.65 |
| | 120 | 119.68 | 120 | 0.32 | 119.84 | | 119.58 | 120.1 | |
| SW24 | 100 | 99.75 | 100 | 0.25 | 99.875 | 1.85 | 99.65 | 100.1 | 1.65 |
| | 102 | 101.85 | 102.03 | 0.18 | 101.94 | 4.24 | 101.75 | 102.13 | 4.04 |
| | 106 | 106.27 | 106.36 | 0.09 | 106.32 | 1.16 | 106.17 | 106.46 | 0.96 |
| | 108 | 107.52 | 108.43 | 0.91 | 107.98 | 5.51 | 107.42 | 108.53 | 5.31 |
| | 114 | 113.94 | 114.75 | 0.81 | 114.35 | 1.55 | 113.84 | 114.85 | 1.35 |
| | 116 | 116.3 | 116.64 | 0.34 | 116.47 | 3.63 | 116.2 | 116.74 | 3.43 |
| | 120 | 120.27 | 120.65 | 0.38 | 120.46 | 3.79 | 120.17 | 120.75 | 3.59 |
| | 125 | 124.44 | 124.64 | 0.2 | 124.54 | 1.84 | 124.34 | 124.74 | 1.64 |
| | 127 | 126.48 | 126.79 | 0.31 | 126.64 | | 126.38 | 126.89 | |
| TNFB | 162 | 161.29 | 162.95 | 1.66 | 162.12 | 1.32 | 161.19 | 163.05 | 1.12 |
| | 165 | 164.27 | 165.45 | 1.18 | 164.86 | 1.82 | 164.17 | 165.55 | 1.62 |
| | 168 | 167.27 | 168.47 | 12 | 167.87 | 5.58 | 167.17 | 168.57 | 5.38 |
| | 174 | 174.05 | 174.24 | 0.19 | 174.15 | 2.93 | 173.95 | 174.34 | 2.73 |
| | 177 | 177.17 | 177.17 | 0 | 177.17 | 2.05 | 177.07 | 177.27 | 1.85 |

TABLE 3-continued

Allele bin ranges used in Traceability analyses.

|  | allele number | observed | range | length of range | range midpoint | observed distance to next allele | defined range (=observed + or − .10) | | defined distance to next allele |
| --- | --- | --- | --- | --- | --- | --- | --- | --- | --- |
|  | 180 | 179.22 | 179.86 | 0.64 | 179.54 | 5.05 | 179.12 | 179.96 | 4.85 |
|  | 186 | 184.91 | 186.36 | 1.45 | 185.64 | 1.68 | 184.81 | 186.46 | 1.48 |
|  | 189 | 188.04 | 189.09 | 1.05 | 188.57 | 10.61 | 187.94 | 189.19 | 10.41 |
|  | 200 | 199.7 | 200.69 | 0.99 | 200.20 |  | 199.6 | 200.79 |  |
| SW122 | 117 | 116.78 | 117.04 | 0.26 | 116.91 | 2.08 | 116.68 | 117.14 | 1.88 |
|  | 119 | 119.12 | 119.12 | 0 | 119.12 | 1.47 | 119.02 | 119.22 | 1.27 |
|  | 121 | 120.59 | 121.48 | 0.89 | 121.035 | 1.51 | 120.49 | 121.58 | 1.31 |
|  | 123 | 122.99 | 123.48 | 0.49 | 123.235 | 1.48 | 122.89 | 123.58 | 1.28 |
|  | 125 | 124.96 | 125.57 | −0.61 | 125.265 | 1.42 | 124.86 | 125.67 | 1.22 |
|  | 127 | 126.99 | 127.71 | 0.72 | 127.35 | 1.67 | 126.89 | 127.81 | 1.47 |
|  | 130 | 129.38 | 129.87 | 0.49 | 129.625 | 1.7 | 129.28 | 129.97 | 1.5 |
|  | 132 | 131.57 | 131.83 | 0.26 | 131.7 |  | 131.47 | 131.93 |  |
| SW2411 | 193 | 192.94 | 192.94 | 0 | 192.94 | 7.32 | 192.84 | 193.04 | 7.12 |
|  | 201 | 200.26 | 200.95 | 0.69 | 200.605 | 3.08 | 200.16 | 201.05 | 2.88 |
|  | 204 | 204.03 | 204.6 | 0.57 | 204.315 | 3.24 | 203.93 | 204.7 | 3.04 |
|  | 208 | 207.84 | 208.58 | 0.74 | 208.21 | 1.14 | 207.74 | 208.68 | 0.94 |
|  | 210 | 209.72 | 210.4 | 0.68 | 210.06 | 1.42 | 209.62 | 210.5 | 1.22 |
|  | 212 | 211.82 | 212.1 | 0.28 | 211.96 | 15.19 | 211.72 | 212.2 | 14.99 |
|  | 227 | 227.29 | 227.29 | 0 | 227.29 |  | 227.19 | 227.39 |  |
| SW857 | 146 | 145.13 | 146.13 | 1 | 145.63 | 5.72 | 145.03 | 146.23 | 5.52 |
|  | 152 | 151.85 | 152.2 | 0.35 | 152.025 | 1.16 | 151.75 | 152.3 | 0.96 |
|  | 154 | 153.36 | 154.3 | 0.94 | 153.83 | 1.38 | 153.26 | 154.4 | 1.18 |
|  | 156 | 155.68 | 156.35 | 0.67 | 156.015 | 1.41 | 155.58 | 156.45 | 1.21 |
|  | 158 | 157.76 | 158.37 | 0.61 | 158.065 | 1.16 | 157.66 | 158.47 | 0.96 |
|  | 160 | 159.53 | 160.38 | 0.85 | 159.955 | 1.68 | 159.43 | 160.48 | 1.48 |
|  | 162 | 162.06 | 162.69 | 0.63 | 162.375 |  | 161.96 | 162.79 |  |
| SW1430 | 167 | 167.07 | 167.71 | 0.64 | 167.39 | 1.35 | 166.97 | 167.81 | 1.15 |
|  | 169 | 169.06 | 169.61 | 0.55 | 169.335 | 2.21 | 168.96 | 169.71 | 2.01 |
|  | 172 | 171.82 | 172.47 | 0.65 | 172.145 | 0.63 | 171.72 | 172.47 | 0.63 |
|  | 173 | 173.1 | 173.45 | 0.35 | 173.275 | 3.59 | 173.1 | 173.55 | 3.39 |
|  | 177 | 177.04 | 177.04 | 0 | 177.04 |  | 176.94 | 177.14 |  |
| SW936 | 100 | 100 | 100.55 | 0.55 | 100.275 | 1.45 | 99.9 | 100.65 | 1.25 |
|  | 102 | 102 | 102.69 | 0.69 | 102.345 | 1.33 | 101.9 | 102.79 | 1.13 |
|  | 104 | 104.02 | 104.65 | 0.63 | 104.335 | 5.64 | 103.92 | 104.75 | 5.44 |
|  | 111 | 110.29 | 110.94 | 0.65 | 110.615 | 5.52 | 110.19 | 111.04 | 5.32 |
|  | 117 | 116.46 | 117.11 | 0.65 | 116.785 | 1.43 | 116.36 | 117.21 | 1.23 |
|  | 119 | 118.54 | 119.18 | 0.64 | 118.86 |  | 118.44 | 119.28 |  |

What is claimed is:

1. A method of tracing an animal product to its system or farm of origin comprising:
   obtaining a sample of said animal product;
   genotyping said animal product utilizing a DNA marker based system to obtain genotyping information;
   comparing the genotyping of said animal product to a reference database, wherein said reference database consists of DNA marker profiles of parental animals unique to a system or farm, or to different systems or farms; and
   analyzing said genotyping information with said reference database to determine a system or farm of origin for said product.

2. The method of claim 1 wherein said genotyping is selected from the group consisting of microsatellites, single nucleotide polymorphisms, amplified fragment length polymorphism and deletions and insertions of all, or part of said DNA marker profile.

3. The method of claim 1 wherein said DNA marker based system comprises the identification of between 10 and 100 microsatellite markers to identify a selected animal product to originate from inside or from outside the controlled system or farm of origin.

4. The method of claim 3 wherein said DNA marker based system further comprises the identification of between 20 and 50 microsatellite markers to identify a selected animal product to originate from inside or from outside the controlled system or farm of origin.

5. The method of claim 1 wherein said animal product information contains information selected from the group consisting of sample date, animal location, animal status, sample shipping information and sample storage information as well as animal phenotype information.

6. The method of claim 1 wherein said animal product is a farmed animal species.

7. The method of claim 1 wherein said animal is selected from the group consisting of: bovine, porcine, poultry, ovine, goats, fish, shellfish, and shrimp.

8. A system for genetically identifying a farm or system of origin of an animal from which an animal product is derived comprising:
   genotyping information of said animal Product utilizing a DNA marker based system;
   comparative data on the genotyping information of said animal product with known animal genotypes in a reference database said reference database consisting of genotype information of parental animals that is unique to each system or farm; and
   analytical data comprising locating matching genotypes in said reference database to identify the system or farm of origin of said animal.

9. The system of claim 8 wherein said animal product information contains information selected from the group consisting of sample date, animal location, animal status, sample shipping information and sample storage information as well as animal phenotype information.

10. The system of claim 8 wherein the genotyping information is selected from the group consisting of genetic mapping, genetic background, genetic screening related to said parental animals or said parental animal samples.

11. The system of claim 8 wherein said genotyping information is selected from the group consisting of microsatellites, single nucleotide polymorphisms, amplified fragment length polymorphism and deletions and insertions of all, or part of said DNA marker profile.

12. The system of claim 8 wherein said DNA marker based system comprises between 10 and 100 microsatellite markers to identify a selected animal product to originate from inside or from outside the controlled system or farm of origin.

13. The system of claim 12 wherein said DNA maker based system further comprises between 20 and 50 microsatellite markers to identify a selected animal product to originate from inside or from outside the controlled system or farm of origin.

14. The system of claim 8 wherein said animal product is a farmed animal species.

15. The system of claim 8 wherein said animal is selected from the group consisting of bovine, porcine, poultry, ovine, goats, fish, shell fish, and shrimp.

16. A method of tracing an animal product to its system or farm of origin comprising:
   obtaining a sample of said animal product;
   genotyping said animal product utilizing a DNA marker based system to obtain genotyping information;
   comparing the genotyping information of said animal product to a reference database, wherein said reference database consists of DNA marker profiles of sires unique to different systems or farms; and
   analyzing said genotyping information with said reference database to determine a system or farm of origin for said product.

* * * * *